(12) United States Patent
Greenfield

(10) Patent No.: US 7,904,969 B2
(45) Date of Patent: Mar. 15, 2011

(54) MED READY GLOVES

(76) Inventor: Carolanne Marie Greenfield, Grand Rapids, MI (US)

( * ) Notice: Subject to any disclaimer, the term of this patent is extended or adjusted under 35 U.S.C. 154(b) by 459 days.

(21) Appl. No.: 11/608,347

(22) Filed: Mar. 31, 2008

(65) Prior Publication Data

US 2009/0241237 A1     Oct. 1, 2009

(51) Int. Cl.
*A41D 19/00*     (2006.01)

(52) U.S. Cl. .................. 2/160; 2/159; 2/161.7; 2/161.6; 2/164

(58) Field of Classification Search ............... 2/159, 160, 2/161.7, 167, 161.6, 164, 158, 16; 424/402
See application file for complete search history.

(56) References Cited

U.S. PATENT DOCUMENTS

| | | | | |
|---|---|---|---|---|
| 5,867,829 A | * | 2/1999 | Hegoas et al. ................... | 2/159 |
| 6,257,785 B1 | * | 7/2001 | Otten et al. ....................... | 401/7 |
| 6,968,808 B2 | * | 11/2005 | Claire ............................. | 119/652 |
| D549,929 S | * | 9/2007 | Schuller et al. ................. | D2/617 |

\* cited by examiner

*Primary Examiner* — Gary L. Welch
*Assistant Examiner* — Alissa J Tompkins
(74) *Attorney, Agent, or Firm* — Kane & Co., PLC

(57) ABSTRACT

This invention comprises of one-time single-use gloves made from latex or vinyl that have a built in pocket space on the outside surface (the term "outside surface" refers to the surface of the glove that is distal from the body of the wearer) of the glove in palm and fingers areas that have tiny surface holes on the outside surface of the pocket to allow dispensing of solution that is sealed under a plastic pull back tab. Once the tab is pulled back, the solution can be forced out of the pocket's tiny holes located on the outside surface of the pocket, by squeezing the hands gently for small amounts or firmly to allow larger amounts of solution. These gloves can be produced to be sterile or non-sterile, depending on the need of the product. The purpose of these gloves are to provide a one time use solution to administering topical solutions, medication and shampoos to human and animal patients, providing a sterile approach when necessary, provide a barrier to disease between the caregiver and patient. They are environmentally friendly by eliminating excessive waste of one time used contaminated containers.

9 Claims, 1 Drawing Sheet

MED READY GLOVES

BACKGROUND OF THE INVENTION

Field of the Invention

The invention relates to the field of dispensers, and particularly to a glove that dispenses a medication, an emollient, shampoo or other solutions through holes in a pocket in the palm area of the glove, and provides a barrier to disease and bodily fluids between the caregiver and the patient.

BRIEF SUMMARY OF THE INVENTION

In accordance with one embodiment of the invention, a glove comprises a one time single use latex or vinyl glove having a built-in latex or vinyl pocket space on the outside surface in the palm and fingers area. Small holes in the pocket allow the dispensing of a solution from the sealed pocket on the outside surface under a plastic pull back tab that when pulled back, the solution can be forced out of the pocket through the holes by squeezing the fingers and hands gently for small amounts of the solution or firmly to allow larger amounts of the solution to dispense. Dispensing of the solution is activated by pulling back a seal covering the pocket comprised of a plastic adhered to the palm outside surface area of the glove.

In another form of the invention, the glove containing pockets in the palm may be made of vinyl or latex and can be produced to be sterile or non-sterile, depending on the need of the product. The purpose of the gloves is to provide a one-time use solution to administering topical solutions, medication and shampoos to humans and animals, provide a sterile approach and barrier to disease, bodily fluids and communicable disease between the caregiver and patient.

An advantage of the invention is that the gloves are environmentally friendly. The glove eliminates the excessive waste of products in hospitals, medical centers and veterinarian clinics. Once certain traditional dispensers for medications, solutions and shampoo containers are opened they have to be disposed of and can not be used on another patient due to contamination. With the glove of the invention, the pockets would hold the desirable amount of solution needed for each patient, provide a barrier, provide sterilization when applicable, and after the patient is treated, the gloves can be disposed of. Previously wasted barely used bottles and containers of each item would not be wasted and only the amount of waste from the glove worn would be disposed of, eliminating huge amounts of waste. The glove would be manufactured in the same manner as the typical medical gloves, but would be revised to include the pocket and then filled with the specific solution needed. The gloves would be useful in the medical, veterinarian and public sector providing a wide range of solutions to be filled in the pockets for use. There are many possibilities for using these gloves with the sealed pockets of solution. Reducing the risk of acquiring potential disease, creating sterile contact and eliminating waste of products are examples of the benefits of these gloves with sealed palm pockets.

DESCRIPTION OF THE INVENTION

Figure 1:
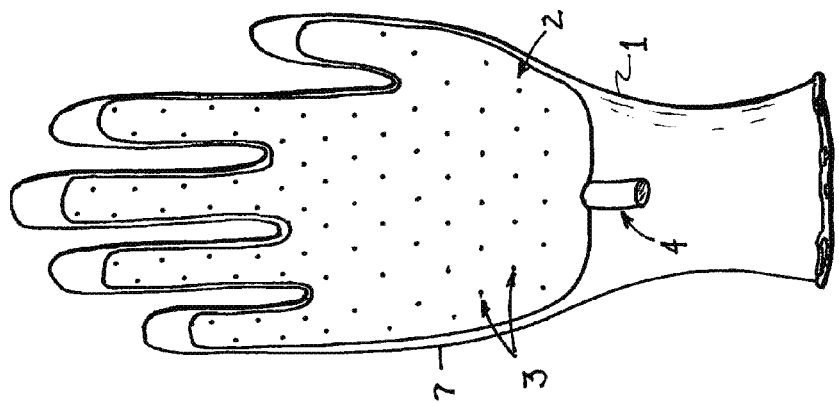
FIG. 1 is a palm view of the glove showing the appearance and placement of the pocketed area in the palm of the glove and the filling valve stem location on the glove according to the preferred embodiment of the invention.

FIG. 1 is a plan view of a standard medical glove demonstrated by the dotted outline 1 of the glove. The right and left glove are mirror images of one another, hence only the right is shown. The glove has a 2 sealable pocket overlying the outer surface palm and fingers areas of the glove. The tiny holes 3 are located on the outer surface of the pocket over the palm and fingers areas of the glove. The filling valve and stem 4 is located on the lower border of the palm area on the outer surface of the pocket. The right and left glove are mirror images of one another, hence only the right is shown.

Figure 2:
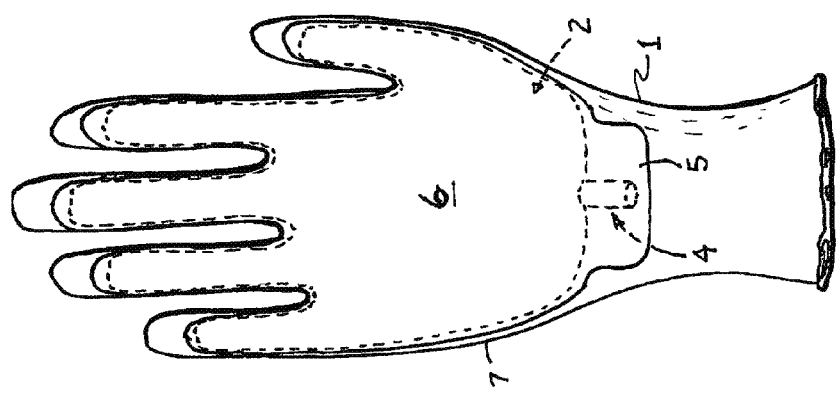
FIG. 2 is a palm view of the glove showing the area to be sealed over the fill-able pocket and the tabbed pull back seal placement on the glove according to the preferred embodiment of the invention.

FIG. 2. is a plan view of a standard medical glove demonstrated by the dotted outline 7 of the glove. The pull back tabbed portion of the seals is located at the bottom palm area over the filling valve stem of the gloves. The pull tab will be attached as one piece to the actual plastic seal. The seal 6 will cover the palm and fingers areas on the outer surface of the pocket to be filled. The right and left glove are mirror images of one another, hence only the right is shown.

One example of use would be to have the appropriate medication used to treat a staph infection in the pocket of the glove. The caregiver would not want skin-to-skin contact with the patient. The caregiver could put on the glove, pull back the tab, squeeze the hand and fingers to force the medication through the holes in the pocket or membrane, apply treatment and throw the glove away. No wasted bottle, no skin contact, time saved and less mess.

Another example would be in the veterinary field. Pet owners can use the glove to apply flea medications or other medication to their pet by gently petting and rubbing the medication on the animal by squeezing the gloves as they are applying the product with no fear placed on the pet. For instance, pets are frightened by the sight, smell or sound of containers used to applying flea medication. These gloves would eliminate the fright and along with, give a soothing massage type of application of flea medication or other topical medications and solutions.

The public can benefit by using the glove to apply medications on children/humans discreetly and without scaring them. The pocket could contain teething medication so a baby can get the medication rubbed on their gums without being exposed to germs. The glove may be useful in shampooing or bathing humans with readily available soap or applying topical medications or solutions and be convenient to dispose of without having to have skin-to-skin contact with a patient who is contagious.

It will become readily appreciated by those skilled in the art that modifications may be made to the invention without departing from the concept disclosed herein. Such modifications are to be considered as included in the following claims, unless these claims by their language expressly state otherwise.

What is claimed:

1. A medical glove for dispensing a topical solution, comprising:
   a glove for fitting over the hand and fingers of a user, said glove including a palm area on an outside surface of said glove;
   a sealable pocket attached to said outside surface of said glove in said palm area of said glove and substantially co-extensive therewith, said sealable pocket including a plurality of holes formed therein adapted to dispense the topical solution there through;

a port attached to and extending from said pocket proximate a hand opening of said glove and adapted to introduce the topical solution into a space defined between said pocket and said outside surface of said palm area; and a detachable seal disposed over an outer surface of said pocket and covering said plurality of holes, said seal having a pull tab disposed over said port.

2. The medical glove as defined in claim 1, wherein said sealable pocket attached to said outside surface of said glove extends along said palm area of a finger area of said glove.

3. The medical glove as defined in claim 2, wherein said sealable pocket extending over said finger area of said glove includes said plurality of holes.

4. The medical glove as defined in claim 3, wherein said detachable seal disposed over said outer surface of said pocket includes on of a sterile seal for preventing contamination of a cavity formed by said pocket and said outside surface said glove.

5. The medical glove as defined in claim 4, wherein said port comprises a filling valve attached to a stem extending from a border between said pocket and said outside surface of said glove.

6. The medical glove as defined in claim 5, wherein said glove for fitting over the hand and fingers of a user includes impermeable gloves barrier intermediate said outside surface of said glove and a user's hand inside said glove.

7. The medical glove as defined in claim 6, further including an adhesive between said detachable seal for adhering said detachable seal to said outer surface of said pocket, sealing said plurality of holes to keep the topical solution in place and to keep the topical solution sterile.

8. A glove for dispensing topical solutions on a patient, comprising:

a glove for placement over a user's hand and fingers, said glove having an inside surface contacting the user's hand and fingers, and an outside surface for engaging a patient while protecting the user's hands from coming into contact with the patient, said outside surface of said glove including a palm side and a back side;

a membrane attached to said palm side of said outside surface of said glove and extending substantially co-extensive with said palm side to form a confined volume between said membrane and said glove, said membrane including a plurality of holes formed therein for permitting passage of the topical solution;

an injection port extending from said glove and in fluid communication with said confined volume for introducing the topical solution into said confined volume; and a detachable seal covering said membrane and said plurality of holes, said seal including a release layer and a pull tab located over said port.

9. A glove for protecting a user's hands while applying a topical compound, comprising:

a glove portion for receiving a user's hands and fingers, said glove including a palm portion and a back portion corresponding generally to a user's palm and back of the user's hand, said glove made from one of vinyl and latex;

a perforated membrane made from one of vinyl and latex attached to an exterior surface of said palm portion of said glove in an area substantially co-extensive with the user's palm and fingers, said membrane defining a fixed volume in a space between said membrane and said exterior surface of said palm portion of said glove;

a valve stem in fluid communication with said fixed volume in said space between said perforated membrane and said exterior surface of said palm portion for introducing the topical compound into said fixed volume; and a removable seal layer disposed over said perforated membrane and retaining any topical compound within said fixed volume and contained in said space between said perforated membrane and said exterior surface of said palm portion.

\* \* \* \* \*